United States Patent [19]

Sunderland

[11] Patent Number: 5,000,167
[45] Date of Patent: Mar. 19, 1991

[54] BLOOD COLLECTION TUBE HOLDER SAFETY GUARD

[75] Inventor: Richard A. Sunderland, Creve Coeur, Mo.

[73] Assignee: Sherwood Medical Company, St. Louis, Mo.

[21] Appl. No.: 389,018

[22] Filed: Aug. 3, 1989

[51] Int. Cl.⁵ .............................................. A61M 5/32
[52] U.S. Cl. ................................... 128/763; 128/764; 604/192; 604/194
[58] Field of Search ............................... 128/760–766; 604/192, 403, 411–415, 195–200

[56] References Cited

U.S. PATENT DOCUMENTS

| | | | |
|---|---|---|---|
| 2,727,517 | 12/1955 | Wilkin | 128/276 |
| 3,304,934 | 2/1967 | Bautista | 128/2 |
| 3,503,386 | 3/1970 | Pieratt | 128/2 |
| 3,520,292 | 7/1970 | Barr, Sr. et al. | 128/2 |
| 3,820,541 | 6/1974 | Langan | 128/215 |
| 4,060,073 | 11/1977 | Collica et al. | 128/1.1 |
| 4,166,450 | 9/1979 | Abramson | 128/764 |
| 4,643,199 | 2/1987 | Jennings, Jr. et al. | 128/763 |
| 4,653,513 | 3/1987 | Dombrowski | 128/765 |
| 4,679,571 | 7/1987 | Frankel et al. | 128/764 |
| 4,731,059 | 3/1988 | Wanderer et al. | 604/192 |
| 4,782,841 | 11/1988 | Lopez | 128/164 |
| 4,787,891 | 11/1988 | Levin et al. | 604/136 |
| 4,788,986 | 12/1988 | Harris | 128/763 |
| 4,790,330 | 12/1988 | Schwobell et al. | 128/764 |
| 4,822,343 | 4/1989 | Beiser | 604/187 |
| 4,844,089 | 7/1989 | Roberti | 128/764 |

FOREIGN PATENT DOCUMENTS

| | | | |
|---|---|---|---|
| 1278387 | 10/1967 | France | 128/764 |
| 7535556 | 6/1977 | France | |
| 2154562 | 9/1985 | United Kingdom | |

Primary Examiner—Robert A. Hafer
Assistant Examiner—Kerry Owens
Attorney, Agent, or Firm—Andrew J. Beck; Montgomery W. Smith; Richard D. Allison

[57] ABSTRACT

A medical device particularly adpated for use with a blood collection tube including a nonlinear needle having first and second needle points wherein the first needle point is selectively protected by a movable protective shield and the second needle point is designed to pierce the stopper of an evacuated blood collection tube. The needle guard is movable axially along a portion of the nonlinear needle between a needle tip exposing retracted position and a needle covering locked extended position.

26 Claims, 8 Drawing Sheets

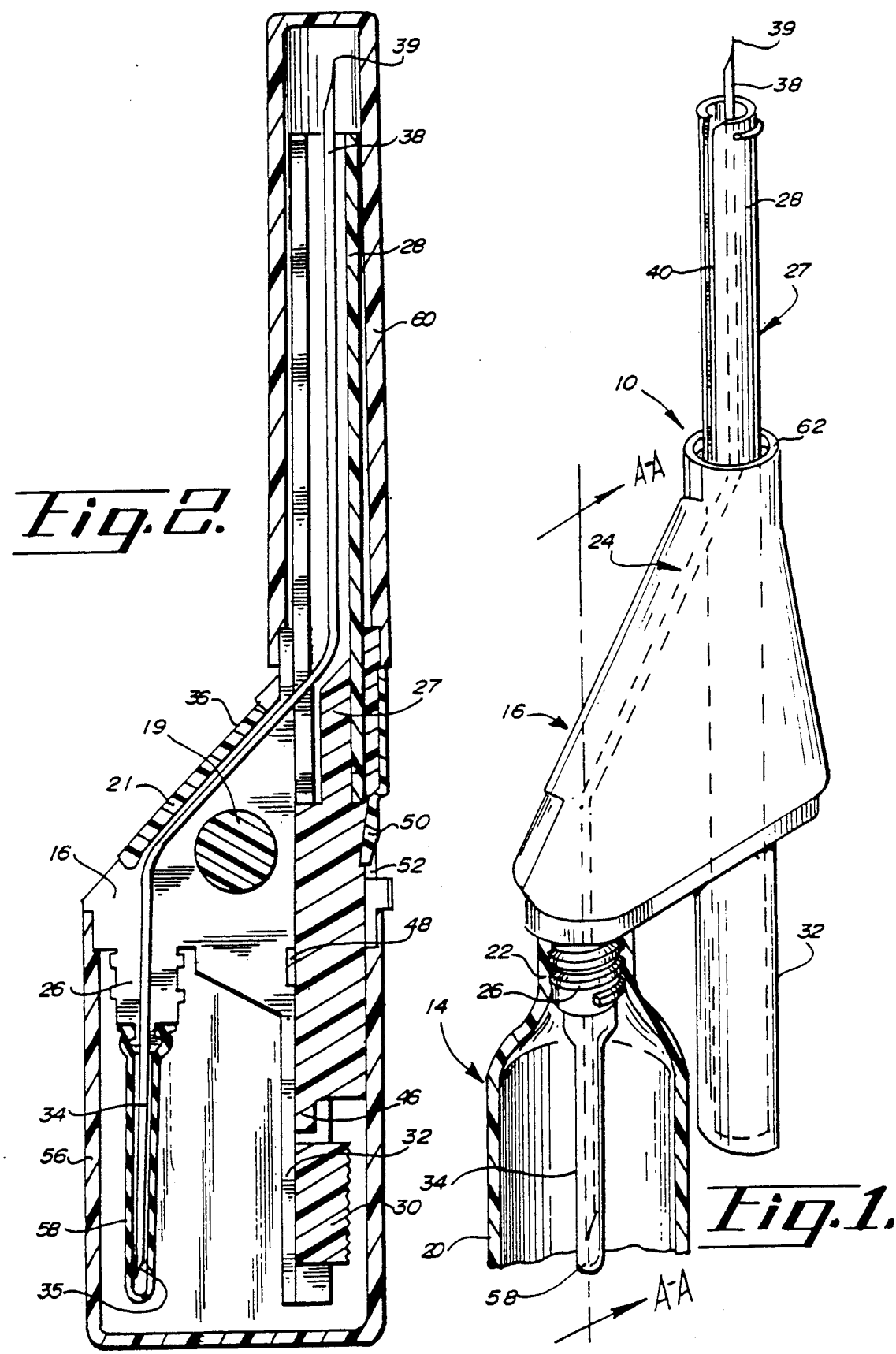

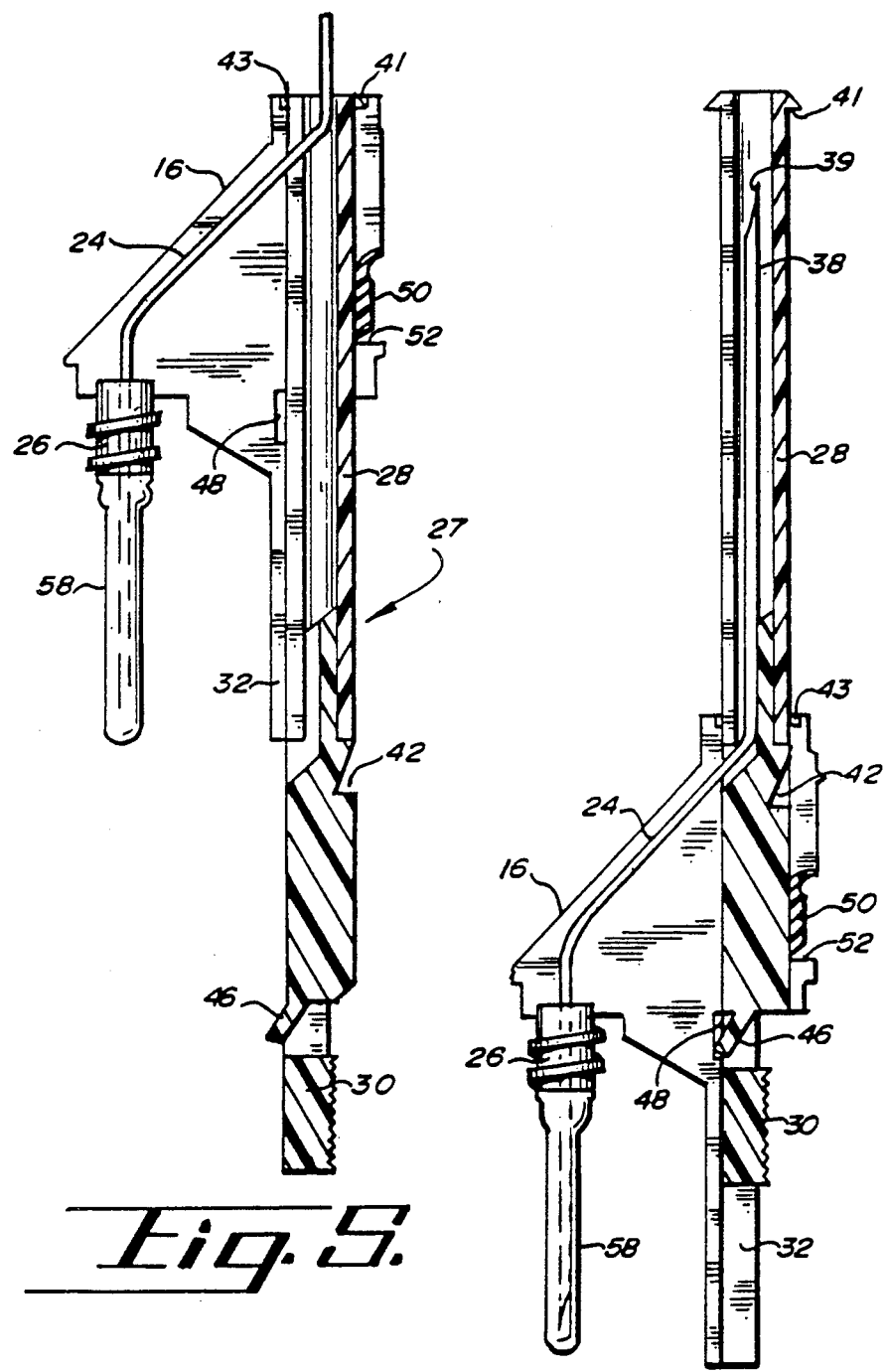

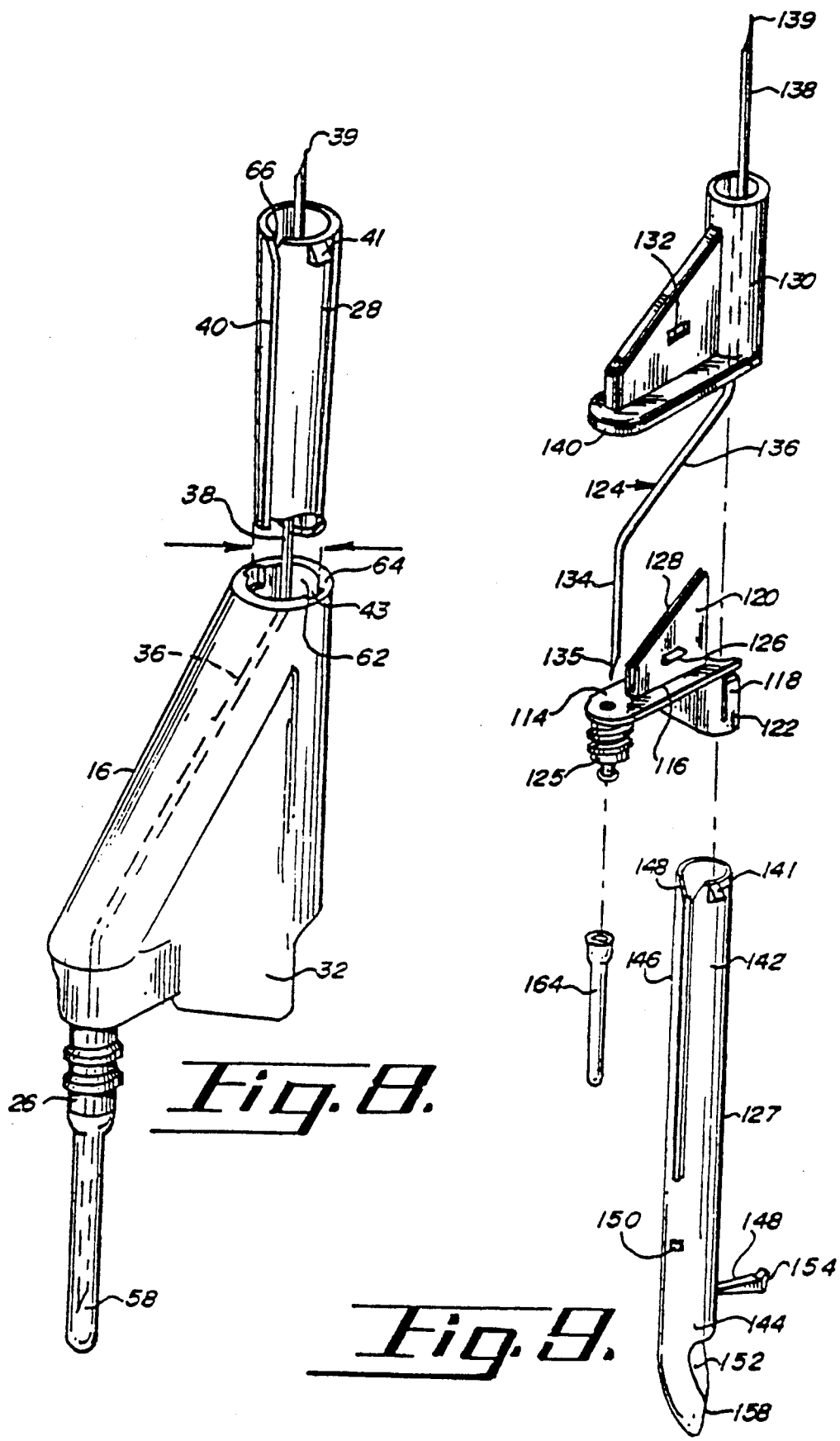

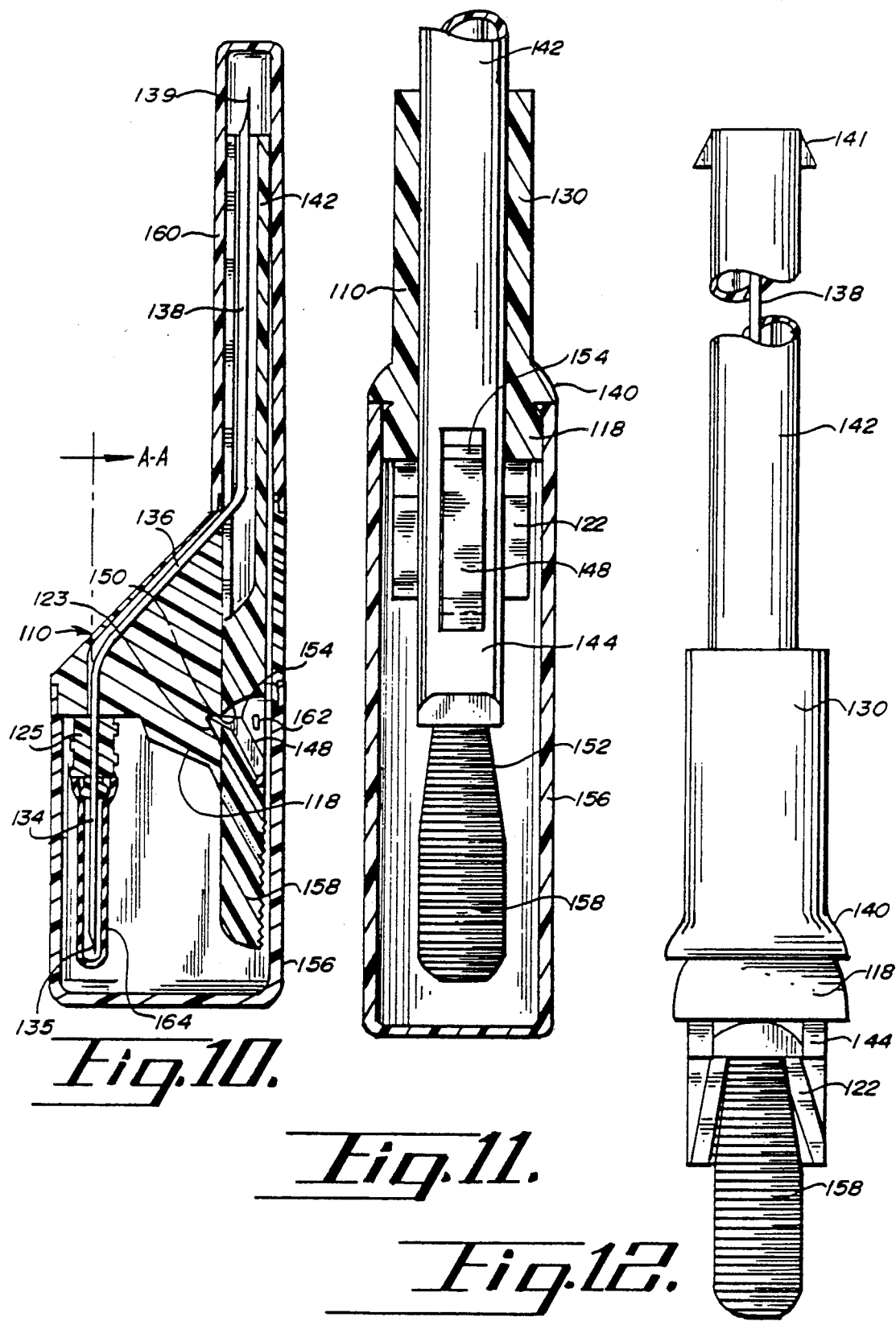

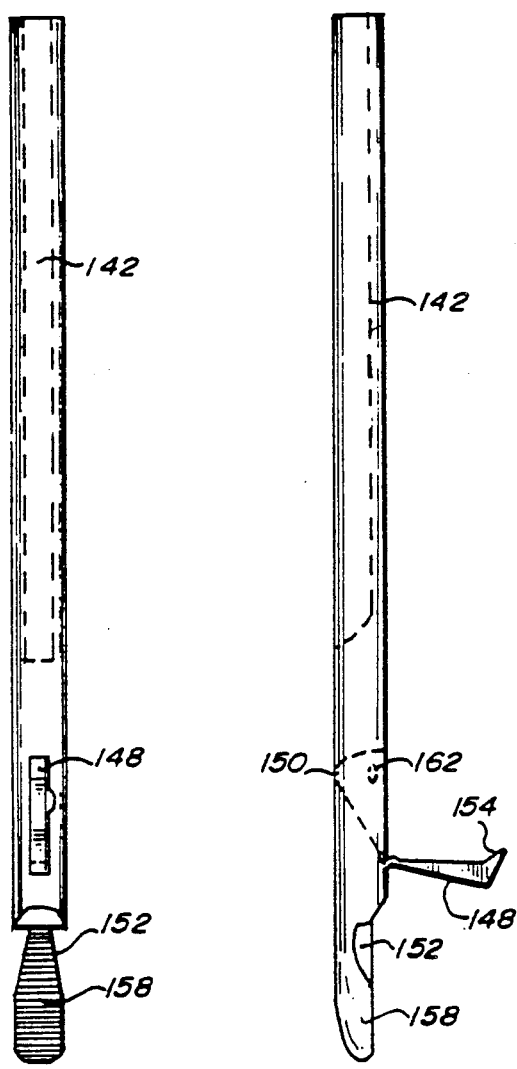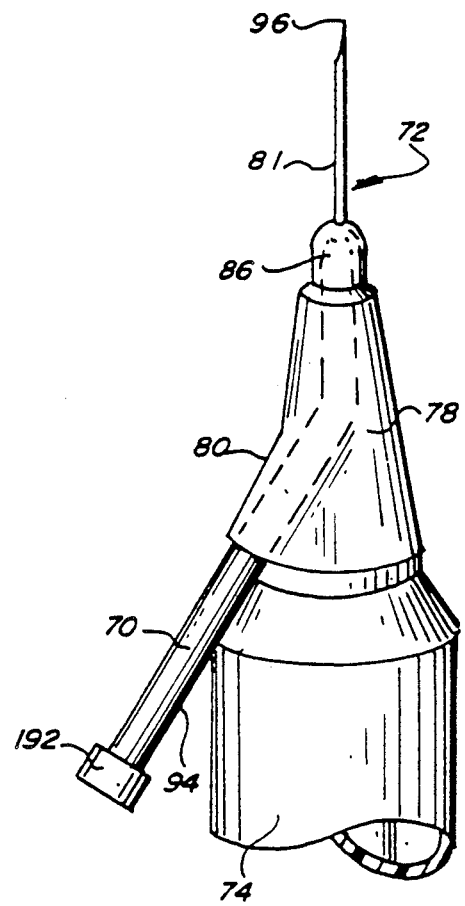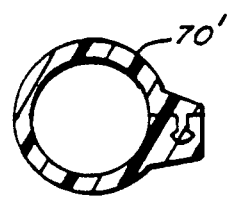

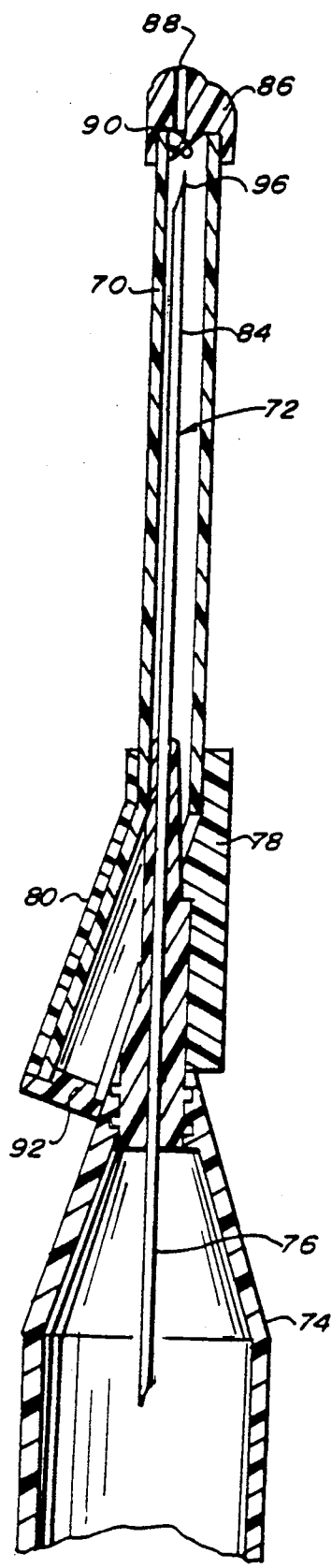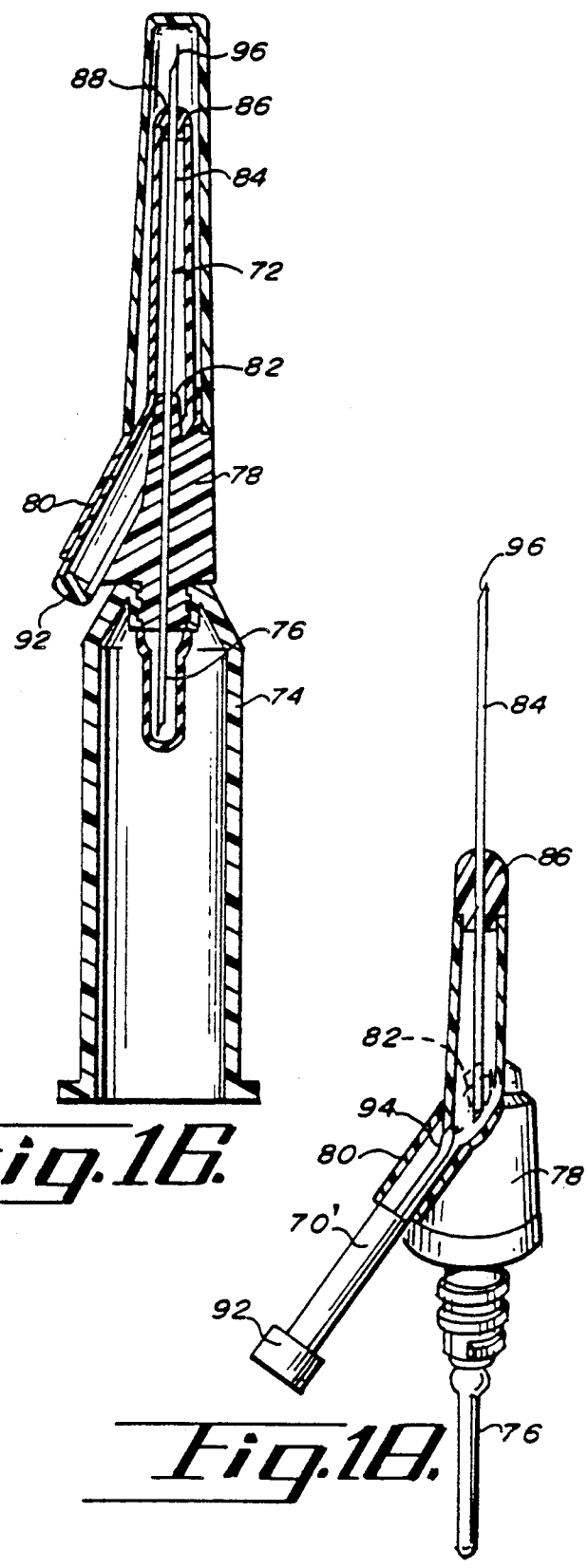
Fig.16.
Fig.17.
Fig.18.

BLOOD COLLECTION TUBE HOLDER SAFETY GUARD

FIELD OF THE INVENTION

This invention relates to blood collection devices and more particularly to a blood collection device having an extendable needle guard thereon for preventing accidental needle sticks.

BACKGROUND OF THE INVENTION

The use of evacuated tubes for the collection of blood samples is well known. Conventional blood collection devices include a cylindrical container or blood collection tube, a blood collection tube holder and a double ended needle. The blood collection tube includes a closed bottom end and an open top end which is sealed by a needle-pierceable stopper or closure. The blood collection tube holder includes an elongate barrel section, a proximal finger flange and a distal needle hub mounting section.

In a conventional blood collection device, the evacuated blood collection tube is removably mounted in the elongate tubular blood collection tube holder. The distal end of the blood collection tube holder includes a threaded hub section which releaseably engages the threaded hub of the double-ended needle. The needle of the conventional blood collection device is typically straight and includes distal and proximal needle sections wherein the distal section of the needle is designed to pierce the vein of the patient and the proximal section of the needle is designed to pierce the stopper of the evacuate collection tube.

Typically, blood is withdrawn from a patient by first puncturing a vein with one end of the double-ended needle and then, while firmly holding the blood collection tube holder, pushing the needle pierceable stopper of the blood collection tube against the other end of the needle until the stopper is pierced. After the desired volume of blood is drawn from the patient's vein into the blood collection tube, the needle is withdrawn from the patient. In the conventional blood collection device, the needle is then removed from the blood collection tub holder and discarded. A new needle may then be threaded onto the blood collection tube holder and the device is used to obtain another blood sample from another patient.

With the onset of AIDS and other infectious diseases, a variety of devices have been designed to decrease the likelihood that a health care worker will be infected by accidental contact with an infected needle. Even if the health care worker does not actually contract the disease from the infected needle, a large amount of time and money is spent on testing and counseling the health care worker every time the health care worker is inadvertently stuck by a potentially infectious needle.

U.S. Pat. No. 4,758,231, issued to Haber et. al. on July 19, 1988, discloses one approach to protecting the health care worker from accidental needle sticks. In the Haber device, a protective shield surrounds the blood collection tube holder while blood is being drawn from the patient. Once the final blood sample has been obtained, the shield is moved distally along the blood collection tube holder to an extended position wherein the distal end of the standard blood collection needle is covered by the protective shield.

Another approach is generally disclosed in U.S. Pat. No. 4,782,841 issued to Lopez on Nov. 8, 1988 and U.S. Pat. No. 4,731,059 issued to Wanderer et. al. on Mar. 15, 1988. In the Lopez and Wanderer devices, an elongated blood collection needle is used in combination with a blood collection tube holder and protective sleeve. The protective sleeve of the respective devices is mounted directly on the elongate distal section of the needle. In the retracted position, the protective shield exposes the distal end of the needle. In the extended position, the protective shield is moved distally along the needle shaft until the protective shield covers the distal end of the needle whereupon the proximal end of the protective sleeve engages a locking mechanism mounted on the needle shaft.

Although the above described devices satisfy the general requirement that the distal end of the needle be protected by a movable shield, the cost of molding and assembling these devices would result in a final product which is not affordable for many hospitals. Additionally, the protective shield of the Haber device increases the outer circumference of the blood collection assembly so that the health care worker may have difficulty carrying multiple blood collection devices on their tray and the blood collection tube holder is not reusable. The devices disclosed in the Lopez and Wanderer patents require the use of an unusually long needle in order to accommodate mounting the protective shield directly on the distal section of the needle. This dramatically increases the cost of producing a device as disclosed in the respective patents. All of the above described patents also require the health care worker to use both hands in order to extend the protective shield. In the Lopez and Wanderer patents, one of the hands of the health care worker must be placed unacceptably close to the potentially infectious distal end of the needle in order to move the protective shield to the extended position.

U.S. Pat. No. 3,326,206 ('206 patent) issued to Barr et al on June 20, 1967 and U.S. Pat. No. 3,520,292 ('292 patent) issued to Barr et al on July 4, 1970 are generally relevant to the present invention for the disclosure of a blood sampling device having a curved needle generally of the type contemplated by the present invention. The device disclosed in the '206 patent is designed to allow the needle to be mounted in or removed from a needle holder without touching the needle. The blood collection device disclosed in this patent includes a slide element which contacts and retains the needle in the needle holder while the blood collection device is in use and wherein the slide element is movable to allow for the removal of the needle from the needle holder. The device illustrated in the '206 patent provides no protection against accidental needle sticks and may actually contribute to the incidence of potentially dangerous needle sticks by providing a device wherein the entire blood collection needle is designed to be removable from the needle holder. The blood collection device illustrated in the '292 patent utilizes a curved needle and a modified blood collection tube holder. The '292 patent is directed to providing a blood collection device having a removable distal end cap and a movable protective diaphragm on the proximal end of the modified blood collection tube holder to provide a blood collection device which is maintained in a sterile condition during storage and transport. As with the '206 patent, the '292 patent provides no protection against accidental needle sticks and requires the use of a modified, non-reusable blood collection tube holder.

SUMMARY OF THE INVENTION

It is an object of the present invention to provide an effective protective shield for use with conventional blood collection tubes and holders.

It is a further object of the present invention to provide a relatively inexpensive protective shield which provides the health care worker with protection against accidental needle sticks and includes none of the disadvantages mentioned above.

Another object of the present invention is to provide a blood collection assembly wherein the protective shield may be extended or retracted with a single hand.

In accordance with one form of the present invention, an integral needle housing is mountable on the distal end of a standard blood collection tube holder so that the protective shield is generally aligned and movable along a support member on the side of the blood collection tube holder between retracted and extended positions. The needle housing includes a nonlinear needle to provide communication between the evacuated blood collection tube and the vein of the patient.

The needle housing further includes a shield assembly consisting generally of a support member, a finger member and a protective shield wherein the finger member and protective shield are slidable linearly in the support member between a retracted position wherein the needle is exposed and an extended position wherein the needle is covered. The shield assembly also includes a start detent on the support member that allows the finger member and protective shield to be moved only in the proximal direction along the needle to expose the distal end of the needle. In the initial start position, the distal end of the needle is partially covered by the protective shield. As the protective shield is moved proximally from the start position, the start detent is moved from a contacting relation with a start recess on the shield assembly to a neutralized position wherein the start detent is generally planar with the interior surface of the support member.

When the protective shield and finger member are in the fully retracted position, the blood sample may be taken by inserting the distal section of the needle into the vein of the patient and inserting a standard blood collection tube onto the proximal section of the needle. When a satisfactory blood sample has been obtained, the distal section of the needle is withdrawn from the arm of the patient and the health care worker may simultaneously move the protective shield to the locked extended position. Unlike previous blood collection devices, the present invention allows the health care worker to hold the blood collection assembly and move the protective shield to the extended position by merely placing their thumb on the finger means and moving the finger means distally until the protective shield assembly is moved to an extended locked position. Once this occurs, the protective shield will cover the distal section of the needle and may not be moved to the retracted position without the use of excessive force.

In other forms of the invention described herein, the distal end of the protective shield assembly includes a reduced diameter distal opening to compress the protective shield as it moves distally along the distal section of needle. In another form of the invention, the distal end of the protective shield includes a pair of tabs thereon to limit the proximal movement of the protective shield to the fully retracted position. In yet another form of the present invention described herein, the protective shield is slidable in a nonlinear manner between the extended and retracted positions. In all of the forms of the invention described above, it is readily anticipated that the present invention may be readily modified for use on nearly any medical or laboratory device having a needle thereon.

An advantage of the present invention is that it is relatively inexpensive to manufacture and simple to use.

A further advantage of the present invention is that it offers convenient single handed operation.

A further advantage of the present invention is that it uses conventional blood collection tubes and holders.

A further advantage of the present invention is that the use of the nonlinear needle allows for the convenient alignment of the needle with the vein of the patient.

A further advantage of the present invention is that it allows the health care worker to reuse the conventional blood collection tube holder.

A further advantage of the present invention is that it is compact and allows multiple blood collection devices to be placed on the health care workers tray.

Yet another advantage of the present invention is that it does not require the health care worker to place their hand near the distal needle point to move the protective shield to the extended position.

BRIEF DESCRIPTION OF THE DRAWINGS

FIG. 1 is a perspective view of the preferred embodiment of the present invention;

FIG. 2 is a side view, partially in cross-section of the preferred embodiment in the assembled condition;

FIG. 5 is a partial cross-sectional view of the preferred embodiment in the retracted position;

FIG. 6 is a partial cross-sectional view of the preferred embodiment in the extended position;

FIG. 8 is a perspective view of an alternate embodiment of the present invention;

FIG. 9 is an exploded perspective view of an alternate embodiment of the present invention;

FIG. 10 is a side view in cross-section, of the assembled alternate embodiment illustrated in FIG. 9 with the protective shield in the start position;

FIG. 11 is a partial frontal view, partially in crosssection, of the assembled embodiment illustrated in FIG. 9;

FIG. 12 is a frontal view of the embodiment illustrated in FIG. 9 with the protective shield in the extended position;

FIG. 13 is a frontal view of the shield assembly of the embodiment illustrated in FIG. 9;

FIG. 14 is a side view of the shield assembly and start detent of the embodiment illustrated in FIG. 9;

FIG. 15 is a perspective view of an alternate embodiment of the present invention;

FIG. 16 is a cross-sectional view of the embodiment illustrated in FIG. 15 with the protective shield in the start position;

FIG. 17 is a enlarged cross-sectional view of the needle hub of the embodiment illustrated in FIG. 15 with the protective shield in the extended position;

FIG. 18 is a partial cross-sectional perspective view of an alternate embodiment of the embodiment illustrated in FIG. 15; and FIG. 19 is a cross-sectional view of the protective shield of the embodiment illustrated in FIG. 18.

DETAILED DESCRIPTION OF THE INVENTION

Figure 4A:
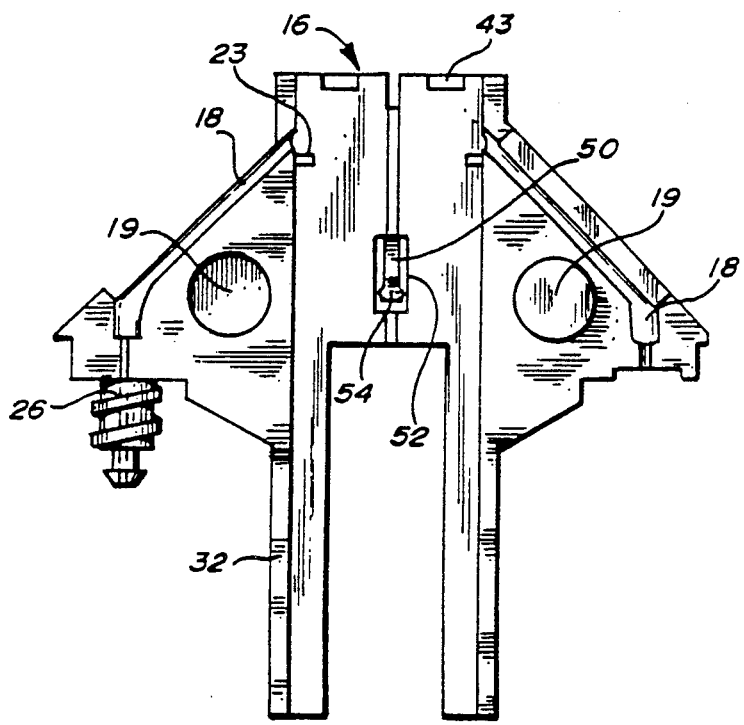
FIG. 4A is a side view of the needle housing of the preferred embodiment illustrating the inside of the needle housing prior to assembly.

In its preferred embodiment, the invention is intended to be used in conjunction with a conventional blood collection tube and holder; however, it is anticipated that the present invention may be modified for use with nearly any medical or laboratory device; such as a syringe, without departing from the contemplated scope of the present invention as defined by the claims attached hereto.

In describing the present invention, the term "distal end" of an element refers to the end of the element closest to the needle point of the device which is designed to pierce the skin of the patient. The term "proximal end" of an element refers to the end of the element furthest from the needle point which is designed to pierce the skin of the patient. The terms "inner" or "inwardly" and "outer" or "outwardly" are used herein to refer to the orientation of an element with respect to the reference plane designated as A—A in FIGS. 1 and 10. The reference plane A—A extends generally through the central axis of the blood collection tube holder and along the proximal needle section.

As illustrated in the attached drawings, the present invention generally includes a blood collection device 10 consisting of a blood collection tube (not shown), a blood collection tube holder 14 and a needle housing 16. The blood collection tube described herein is a conventional evacuated tube having a needle pierceable stopper thereon. The blood collection tube holder 14 described herein is a conventional blood collection tube holder consisting of a pair of proximal finger flanges (not shown), an elongate barrel section 20 and a preferably threaded needle hub mounting section 22 positioned on the distal end of the blood collection tube holder 14.

Figure 4B:
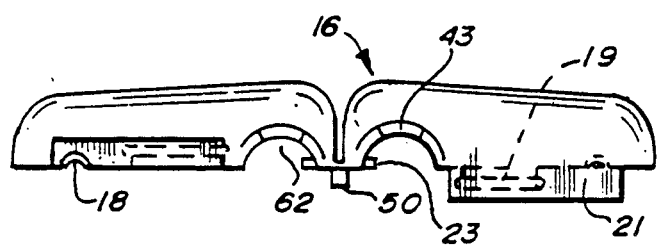
FIG. 4B is a top view of the needle housing illustrated in FIG. 4A.

In the preferred embodiment, the needle housing 16 preferably consists of a foldable, one-piece molded element which may be molded as illustrated in FIGS. 4A and 4B and then folded and bonded around the nonlinear needle referred to here in as needle 24 to form the needle housing 16 illustrated in FIG. 1. It is anticipated that the needle housing 16 may also be formed by a pair of molded elements bonded together to retain the needle 24 therein. The needle housing 16 as illustrated in FIGS. 4A and 4B, includes a needle recess 18, a bonding surface 19, a needle protecting lip 21 and a shield alignment lip 23. The needle recess 18 is located on each half of the needle housing 16 to retain the needle 24 therein in a fixed position. The bonding surface 19 consists of a protrusion on one of the halves of the needle housing 16 and a matching recess on the other half to irreversibly retain the needle housing 16 in the assembly position. The needle protecting lip 21 extends outwardly from the top of one half of the needle housing 16 in an overlapping manner into a corresponding recess on the opposing half of the needle housing 16 to maintain the sterility of the needle 24 and to prevent access to the needle 24 when the needle housing 16 is assembled. The shield alignment lip 23 extends into the cylindrical shield support member 32 to contact the elongate slit 40 on the protective shield 28 to prevent rotational movement of the protective shield 28 as it is moved between the retracted and extended positions.

The assembled needle housing 16 preferably includes the nonlinear needle 24, a needle hub section 26, a shield support member 32 and a shield assembly 27 consisting of a protective shield 28 and a finger member 30. The needle 24 of the present invention consists generally of a proximal needle section 34 which is preferably straight and extends proximally beyond the proximal end of the needle hub section 26 to a sharpened proximal point 35; a curved intermediate needle section 36 is contained within the needle hub section 26 to create the preferred nonlinear orientation of the needle 24 and a distal needle section 38 which is preferably straight and extends distally beyond the distal end of the needle hub section 26. The proximal needle section 34 and the distal needle section 38 of the needle 24 are preferably oriented in a generally parallel and offset manner with respect to each other to facilitate single handed operation of the present invention. The distal end of the needle 24 includes a bevelled distal needle point 39 oriented to facilitate the insertion of the distal needle section 38 into the vein of the patient. The proximal needle point 35 on the proximal end of the needle 24 is designed to pierce the stopper of a blood collection tube once the proximal end of the needle hub section 26 has been threaded onto the hub mounting section 22 of the blood collection tube holder 14.

The needle hub section 26 of the present invention preferably consists of a separately molded element having a threaded section thereon to facilitate the attachment of the blood collection tube holder 34 thereto. The needle hub section 26 is preferably adhesively bonded or welded to a recess on the inner, proximal side of the needle housing 16.

The protective shield 28 of the present invention preferably consists of an elongate tubular member constructed of a semi-rigid polypropylene having a sufficient rigidity to protect against being deflected off the distal needle section 38 while having sufficient flexibility to be positioned along the length dimension of the distal needle section 38 in an overlapping or encircling manner. The protective shield 28 includes an elongate slit 40 extending proximally from the distal end thereof to a location approximately midway along the shield assembly 122 and a pair of radial tabs 41 near the distal end of the protective shield 28. The proximal end of the shield assembly 27 includes the finger member 30 which extends proximally from the proximal end of the protective shield 28. The protective shield 28 and finger member 30 are slidably retained in the shield support member 32 and are preferably positioned to slide in the shield support member 32 adjacent to the barrel section 20 of the blood collection tube holder 14. The protective shield 28 is further axially aligned to slide along the distal needle section 38 of the needle 24. Although the shield assembly 27 is preferably constructed as a two-piece molded or extruded element wherein the protective shield 28 and finger member 30 are formed as separate elements which are then assembled together with either a frictional fit, adhesives or nearly any other convenient method of attachment, it is readily anticipated that the shield assembly 27 may also be formed as a single-piece molded or extruded element.

In this embodiment, a generally wedge-shaped start detent recess 42 is positioned on the outer side of the shield support member 32 adjacent to the proximal end of the protective shield 28. A needle recess (not shown) is located near the proximal end of the inner surface of protective shield 28 adjacent to the finger member 30. The needle recess is preferably an enlarged opening on the proximal end of the elongate slit 40 to allow the protective shield to enclose the proximal end of the distal needle section 38 when the protective shield 28 is in the extended position. A biased locking tab 46 is positioned on the inner surface of the shield assembly 27 on the finger member 30. The locking tab 46 is biased inwardly from the finger member 30 to form a contacting relation with a locking recess 48 located on the inner side surface of the shield support member 32 when the protective shield 28 is in the fully extended position.

The shield support member 32 of the shield assembly 27 includes an enclosed elongate groove or channel along the outer side of the needle housing 16 to enclose a portion of the shield assembly 27 therein. The distal end of the shield support member 32 includes an enlarged recess 43 to releasably retain the radial tabs 41 therein when the protective shield 28 is in the retracted position. The proximal end of the shield support member 32 is semicircular and extends beyond the proximal end of the needle housing 16 to allow the shield assembly 27 to be slidably moved therein a sufficient distance to allow the protective shield 28 to expose the distal needle section 38 when the protective shield 28 is moved to the retracted position. The groove or channel section of the shield support member 32 extends to the distal end of the needle housing 16 to form a distal shield opening 62 which is adjacent to the enlarged recess 43 and positioned generally at the intersection of the intermediate needle section 36 and the distal needle section 38.

A locking recess 48 is positioned approximately midway along the inner side surface of the shield support member 32 to retain the locking tab 46 from the shield assembly 27 therein when the protective shield 28 is in the fully extended position. The outer side surface of the shield support member 32 includes an inwardly biased start detent 50. The start detent 50 is positioned in a side recess 52 on the needle housing 16. The proximal end of the start detent 50 preferably includes a pair of contacting lips 42 to frictionally contact the sides of the side recess 52 to retain the start detent 50 in the neutralized position once the shield assembly 27 is moved proximally from the initial start position.

Figure 3:
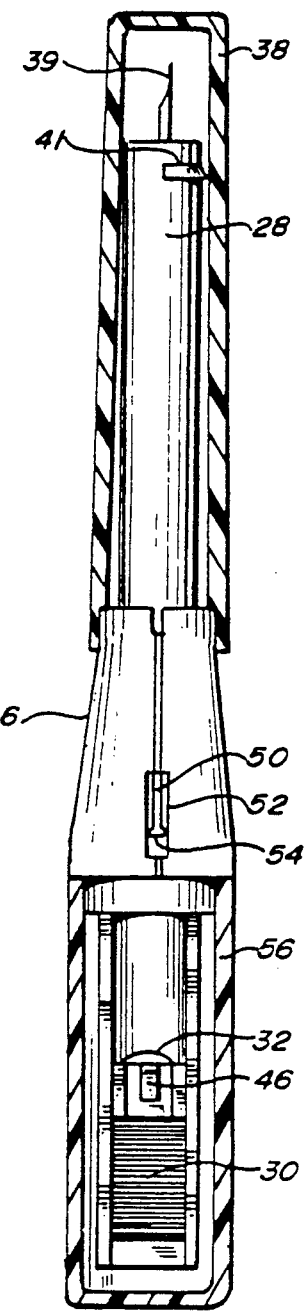
FIG. 3 is a frontal view of the preferred embodiment partially in cross-section.
Figure 7A:
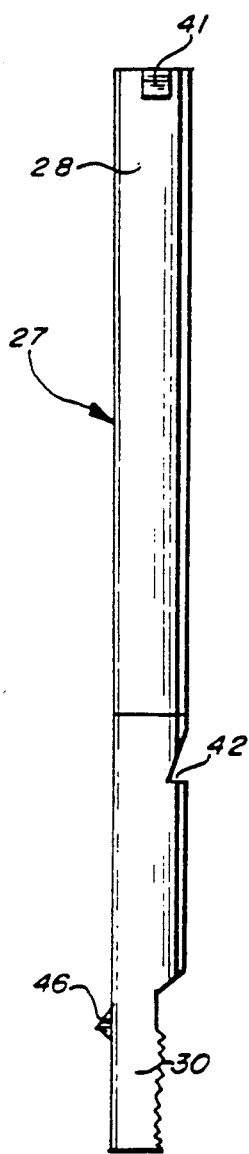
FIG. 7A is a side view of the shield assembly of the preferred embodiment.
Figure 7B:
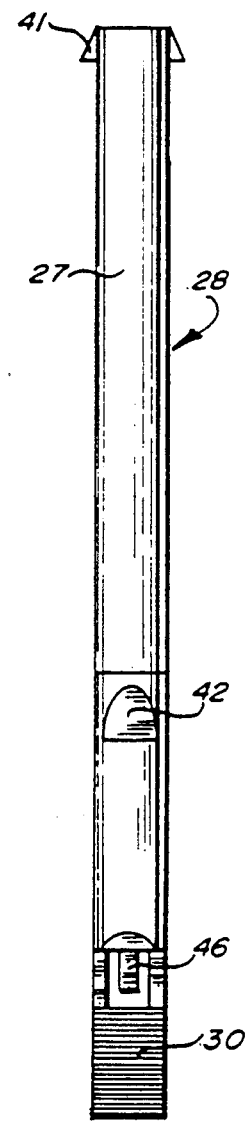
FIG. 7B is a frontal view of the shield assembly of the preferred embodiment.

FIGS. 2 and 3 illustrate the blood collection device 10 of the preferred embodiment assembled for shipping and storage. The proximal end of the blood collection device 10 includes a rectangularly shaped proximal hard case 56 which is preferably heat staked to the needle housing 16. The proximal hard case 56 encloses and maintains the sterility of the proximal end of the shield assembly 27 and the shield support member 32 during shipping and storage. A rubber needle sleeve 58 is also preferably positioned on the proximal needle section 34 to prevent accidental needle sticks when the proximal hard case 56 is removed and prior to the insertion of the proximal needle section 34 into the blood collection tube holder 14. Once the hub mounting section 22 of the blood collection tube holder 14 is threaded into the needle hub section 26 of the needle housing 16, the elongate barrel section 20 of the blood collection tube holder 14 protects the user from accidentally contacting the proximal needle point 35 of the proximal needle section 34. The distal end of the blood collection device 10 includes a distal hard case 60 which is heat staked to the distal end of the needle housing 16. The distal hard case 60 encloses and maintains the sterility of the distal needle section 38 and protects the distal needle point 39 during shipping and storage.

When the health care worker desires to obtain a blood sample from a patient, the health care worker initially applies lateral pressure to the proximal hard case 56 to break the heat stake on the needle housing 16. Next, the blood collection tube holder 14 is threaded onto the needle hub section 26 of the needle housing 16. Once the appropriate site on the patient's arm has been prepared, the health care worker may remove the distal hard case 60 from the needle housing 16 by rotating the distal hard case 60 until the heat stake is broken.

Next, the health care worker moves the shield assembly 27 from the start position wherein the protective shield 28 substantially encloses the distal needle section 38 to the retracted position by placing their thumb on the finger member 30 to move the finger member 30 proximally along the shield support member 32 until the distal needle section 38 is uncovered by the protective shield 28. As the shield assembly 27 is moved proximally along the shield support member 32, the protective shield 28 and the elongate slit 40 are moved over the distal portion of the intermediate needle section 36 and the distal needle section 38. The start detent 50 is also moved from an initial start position in the start detent recess 42 to a neutralized position wherein the contacting lips 54 of the start detent 50 frictionally contact the sides of the side recess 52 to create a generally planar relation along the interior surface of the shield support member 32 so that the start detent 50 does not interfere with any further movement of the shield assembly 27 in the shield support member 32. The shield assembly 27 is moved proximally in the shield support member 32 until the radial tabs 41 reach the enlarged recess 43 which prevents further proximal movement of the shield assembly 27 in the shield support member 32. Once the shield assembly 27 is in the retracted position, the blood collection device 10 and the distal needle section 38 of the needle 24 may then be aligned parallel to the vein of the patient so that the bevelled end of the distal needle point 39 is adjacent to the skin of the patient.

The distal needle section 38 of the needle 24 is then inserted into the vein of the patient and an evacuated blood collection tube is inserted into the blood collection tube holder 14. As the blood collection tube is inserted into the blood collection tube holder 14, the stopper of the blood collection tube contacts the rubber needle sleeve 58 and causes the proximal needle point 35 to pierce the rubber needle sleeve 58. The stopper then compresses the rubber needle sleeve 58 against the needle hub section 26 of the needle housing 16 as the blood collection tube is pushed into the blood collection tube holder 14.

Once the proximal needle section 34 passes through the stopper of the blood collection tube, blood is drawn from the vein of the patient into the evacuated blood collection tube. When a sufficient blood sample has been obtained from the patient, the blood collection tube is removed from the blood collection tube holder 14 and the rubber needle sleeve 58 resiliently covers the proximal needle section 34. If a further blood sample is desired, a second blood collection tube may be inserted into the blood collection tube holder 14 and the blood collection procedure is repeated.

Once a sufficient number of blood samples have been obtained and the final blood collection tube has been removed from the blood collection tube holder 14, the health care worker may remove the distal needle section 38 of the needle 24 from the vein of the patient. Immediately after the distal needle section 38 of the needle 24 has been removed from the vein of the patient, the health care worker may single handedly hold the blood collection device 10 and move the finger member 30 distally along the shield support member 32 until the protective shield 28 encloses the distal needle section 38 and the distal needle point 39 of the blood collection device 10. As the finger member 30 and protective shield 28 are moved distally along the shield support member 32, the inwardly biassed locking tab 46 will frictionally contact the inner surface of the shield support member 32 until the locking tab 46 reaches the locking recess 48 on the inner surface of the shield support member 32 when the protective shield 28 reaches the fully extended position. The locking tab 46 and locking recess 48 are located in an enclosed portion of the needle housing 16 to prevent access to the locking mechanism of the present invention so that the locking mechanism cannot be defeated unless extraordinary force is used.

FIG. 8 illustrates an alternate embodiment of the present invention wherein the shield support member 32 includes a reduced diameter section 64 to compress the protective sheath 28 around the distal needle section 38 as the protective sheath is moved distally from the retracted position to the extended position As illustrated, the reduced diameter section 64 is positioned at the distal shield opening 62 on the needle housing 16 and adjacent to the intersection of the intermediate needle section 36 and the distal needle section 38 to compress the protective shield 28 after the needle 24 has passed through the elongate slit 40. This embodiment provides additional protection against needle sticks caused by accidental deflection of the protective shield 28 off the distal needle section by causing the sides of the protective shield 28 to overlap once the protective shield 28 passes distally beyond the reduced diameter section 64.

FIG. 8 illustrates yet another feature of the present invention wherein the protective shield 28 includes a distal notched section 66 to assist in aligning the needle 24 with the elongate slit 40 and a modified shield support member 32'. In this embodiment, the protective shield 28 is moveable to a retracted position wherein the notched section 66 of the protective shield 28 is spaced apart from the needle 24 a predetermined distance The radial tabs 41 on the distal end of the protective shield 28 contact the enlarged recesses 67 on the distal end of the needle housing 16. This allows the health care worker to visually observe the entire distal needle section 38 of the needle 24 prior to or during the insertion of the needle into the patient while the protective shield 28 is in the retracted position. The modified shield support member 32' is shorter than the shield support member 32 of the previous embodiment and functions as a guide and locking means for the shield assembly 27 in the same manner as described above for FIGS. 1–7.

Another form of the present invention is illustrated in FIGS. 9–14. In this embodiment, the needle housing 110 consists of a pair of preferably molded elements which may be snap fit or adhesively bonded together to retain the nonlinear needle referred to herein generally as needle 124 in a sterile, fixed position within the needle housing 110. The needle housing 110 of this embodiment consists generally of a needle cover 112, a needle platform 114, a shield assembly 127 and a nonlinear needle 124. As with the first embodiment, the needle 124 of the present embodiment, consists of a generally straight proximal needle section 134, a curved intermediate needle section 136 and a generally straight distal needle section 138. The proximal end of the proximal needle section 134 and the distal end of the distal needle section 138 include bevelled needle points, 135 and 139, respectively.

The needle platform 114 of the present embodiment includes a threaded needle hub section 125, a generally flat platform surface 116, a shield locking section 118, and an angled needle positioning surface 120. The needle hub section 125 extends proximally along the inner side of the flat platform surface 116 and includes a threaded proximal section and hub thereon to facilitate the attachment of a standard blood collection tube holder 14 and rubber needle sleeve 164 thereto. The shield locking section 118 extends proximally from the outer side of the flat platform surface 116 to frictionally contact the shield assembly 127. The shield locking section 118 consists of a semi-circular extension having a pair of inwardly biased locking detents 122 on the sides thereof and a ramped start detent recess 123 on the inner surface thereof. The angled positioning surface 120 is a quadrilaterally shaped element which extends distally from the center of the platform surface 116 between needle hub section 126 and the shield locking section 118. The sides of the angled positioning surface 120 include a pair of cover retaining tabs 126 extending outwardly therefrom. The top surface of the angled positioning surface 120 is angled to match the general angle of the intermediate needle section 136 of the needle 124 and includes a needle groove 128 to retain the intermediate needle section 136 of the needle 124 therein.

The needle cover 112 is preferably a molded element which encloses and retains the intermediate needle section 136 of the needle 124 in a fixed position. The outer side of the needle cover 112 includes a cylindrical shield support cylinder 130 which slidably encloses and retains the shield assembly 127 therein The sides of the needle cover 112 include a pair of tab retaining slots 132 which irreversibly retain the tabs 126 from the needle platform 114 therein. A perimeter flange 140 is located along the proximal surface of the needle cover 112. The perimeter flange 140 is spaced slightly above the proximal end of the needle cover 112 to provide support for the proximal hard case 156 which is preferably heat staked thereto.

The shield assembly 127 is generally a rigid elongate tubular element having a distal section 142 and a proximal section 144. The distal section 142 of the shield assembly 127 includes an elongate needle slot 146 extending the entire length of the distal section 142. The distal end of the needle slot 146 includes a notched section 148 to facilitate the passage of the needle 124 into the needle slot 146 and a pair of radial tabs 141 to limit the proximal movement of the shield assembly 127. The proximal section 144 of the shield assembly 127 includes a start detent 148, a start detent slot 150 and a pair of shield locking recesses 152 thereon. The start detent slot 150 is located on the inner surface of the shield assembly 127. The start detent 148 is a generally wedge shaped, moveable element having its proximal end hingedly positioned on the outer surface of the shield assembly 127. The distal end of the start detent 148 includes a positioning tab 154 thereon which is angled inwardly to releasably project through start detent slot 150 and into the start detent recess 123 on the platform surface 116 in the initial assembled position The shield locking recesses 152 are positioned proximal to the start detent 148 and form a pair of generally wedge shaped recesses on the outer proximal surface of the shield assembly 127. The proximal end of the shield assembly 127 forms a finger pad 158 to facilitate the single handed operation of the present embodiment.

Assembly of this embodiment is relatively simple and may be accomplished quickly and inexpensively. Initially, the intermediate needle section 136 of the needle 124 is positioned in the needle groove 138 so that the proximal needle section 134 of the needle 124 extends through the threaded proximal section of the platform surface 116. The needle 124 may be adhesively bonded or welded to any convenient surface of the platform surface 116 to retain the needle 124 therein The needle cover 112 is then snapped onto the platform surface 116 so that the retaining tabs 126 extend through the retaining slots 132 to retain the needle cover 112 on the platform surface 116 and the distal needle section 142 extends through the shield support cylinder 130. The rubber needle sleeve 164 is then placed on the proximal needle section 134 and the shield assembly 127 is inserted into the shield support cylinder 130 on the needle cover 112.

The start detent 148 is then pressed inwardly as the shield assembly 127 is moved distally through the shield support member 130. The shield assembly 127 slides distally through the shield support member 130 until the positioning tab 154 on the start detent 148 passes through the start detent slot 150 and contacts the start detent recess 123 on the shield locking section 118 of the needle platform 114. In this position, the distal section 142 of the shield assembly 127 partially encloses the distal needle section 138 and is prevented from further distal movement by contact between the positioning tab 154 on the start detent 148 and distal side of the start detent recess 123. Finally, the proximal hard case 156 and the distal hard case 160 are heat staked to the respective ends of the assembly. Once the device has been sterilized, it may then be shipped and stored without losing sterility.

The present embodiment operates similar to the first embodiment described above for FIGS. 1-7. When the health care worker desires to obtain a blood sample from a patient, the health care worker may apply lateral pressure to the proximal hard case 156 to break the heat stake between the proximal hard case 156 and the perimeter flange 140. Next, the blood collection tube holder 14 is threaded onto the needle hub section 125. Once the appropriate site on the patients arm has been prepared, the health care worker may remove the distal hard case 160 from the needle housing 110 by rotating the distal hard case 160 until the heat stake on the distal end of the needle cover 112 is broken.

The health care worker may then move the shield assembly 127 from the initial start position to the retracted position by placing their thumb on the finger pad 158 and moving the shield assembly 127 proximally along the shield support member 130. As the shield assembly 127 is moved proximally along the shield support member 130, the start detent 148 is moved from the start detent recess 123 and the start detent slot 150 to a neutralized position on the shield assembly 127. A pair of supplemental detents 162 on the interior surface of the shield assembly 127 prevent the start detent 148 from returning to the initial start position. Once the shield assembly 127 is moved to the retracted position, the blood collection device 10 and the distal needle section 138 of the needle 124 may be aligned parallel to the vein of the patent so that the distal needle point 139 is adjacent to the skin of the patient.

Next, the distal needle section 138 of the needle 124 is inserted into the vein of the patient and an evacuated blood collection tube is inserted into the blood collection tube holder 14. As the blood collection tube is inserted into the blood collection tube holder 14, the stopper of the blood collection tube contacts the rubber needle sleeve 164 and causes the proximal needle point 135 to pierce the rubber needle sleeve 164. The stopper then compresses the rubber needle sleeve 164 against the needle hub section 125 of the needle housing 110 while the stopper is pierced by the proximal needle point 135.

Once the stopper is pierced by the proximal needle point 135, blood is drawn from the vein of the patient into the evacuated blood collection tube 12. When a sufficient amount of blood has been obtained, the blood collection tube 12 is removed from the blood collection tube holder 14 and the resilient rubber sleeve recovers the proximal needle point 135. If a further blood sample is desired, a second blood collection tube 12 may be inserted into the blood collection tube holder 14 and the blood collection procedure is repeated.

Once a sufficient number of blood samples have been obtained and the final blood collection tube 12 has been removed from the blood collection tube holder 14, the health care worker may remove the distal needle section 138 from the vein of the patient. Immediately after removing the needle 124 from the vein of the patient, the health care worker may single handedly hold the blood collection device 10 and move the finger pad 156 distally along the shield support member 130 until the distal section 152 of the shield assembly 127 encloses the distal needle section 138 and distal needle point 139 of the blood collection device 10. As the shield assembly 127 is moved distally along the shield support member 130, the locking detents 122 will be biased against sides of the shield assembly 127 until the locking detents 122 reach the locking recesses 152 on the proximal section 144 of the shield assembly 127. When the shield assembly 127 is in the locked extended position, the cooperation between the locking detents 122 and the locking recesses 152 will prevent the shield assembly 127 from being retracted unless excessive force is applied to the shield assembly 127.

FIGS. 15-19 illustrate yet another form of the present invention wherein the protective shield 70 is slidable in a nonlinear manner along a preferably straight needle 72.

In this embodiment, the blood collection tube holder 74 and the proximal needle section 76 are preferably the same as the blood collection tube holder 14 and the proximal needle section 34 described above. As illustrated in FIG. 16, the needle hub section 78 is threadedly mounted on the distal end of the blood collection tube holder 74 and includes an offset protective shield passageway 80 through which the protective shield 70 is moved between the retracted and extended positions. The distal end of the needle hub section 78 preferably includes a reduced diameter section 82 to compress the protective shield 70 as it passes from the protective shield passageway 80 onto the distal needle section 84 of the needle 72.

The protective shield 70 of the present invention is preferably constructed of a semi-rigid polypropylene having sufficient rigidity to adequately protect the needle while having sufficient flexibility to pass nonlinearly through the protective shield passageway 80. The distal end of the protective shield 70 includes a hardened tip 86 to protect the health care worker from accidental needle sticks. As illustrated in FIG. 17, the hardened tip 86 includes a needle hole 88 and a flexible lip 90 thereon. The proximal end of the protective shield 70 includes a finger member 92 thereon to facilitate the movement of the protective shield 70 between the retracted and extended positions. The elongate slit 94 of this embodiment extends between the hardened tip 86 and the finger member 92 to allow the protective shield 70 to pass over the proximal end of the distal needle section 84.

When the protective shield 70 is in the retracted position, the hardened tip 86 is positioned on the proximal end of the distal needle section 84 immediately adjacent to the distal end of the needle hub section 78 while the finger member 92 extends proximally from the proximal side of the protective shield passageway 80. As the protective shield 70 is moved to the extended position, the hardened tip 86 moves distally along the distal needle section 84 and the elongate slit 94 of the protective shield 70 is opened as it passes over the proximal end of the distal needle section 84. Once the elongate slit 94 has passed over the proximal end of the distal needle section 84, the reduced diameter section 82 of the needle hub section 78 compresses the elongate slit 94 to cause the sides of the protective shield to overlap once they have passed beyond the needle hub section 78.

In the extended position, the hardened tip 86 extends beyond the distal point 96 a sufficient distance to allow the flexible lip 90 to prevent the distal needle point 96 from returning through the needle hole 88. The finger member 92 on the proximal end of the protective shield 70 is positioned adjacent to the proximal end of the protective shield passageway 80 and cannot be retracted unless extraordinary force is used to force the distal needle point 96 through the flexible lip 90 and into the needle hole 88 of the hardened tip 86. In another form of the present embodiment, the finger member 92 is movable into an enlarged area (not shown) in the proximal end of the protective shield passageway 80 so that the finger member is substantially flush with the proximal end of the protective shield passageway 80 in the extended portion.

FIGS. 18 and 19 illustrate yet another alternate form of the protective shield 70 of FIG. 15, wherein the respective sides of the protective shield 70' are oriented in an interlocking relationship once the protective shield 70' pass beyond the proximal end of the distal needle section 84.

The foregoing is intended to be descriptive of the preferred form of the various embodiments described above. It is readily anticipated that certain features of the embodiments are interchangeable or may be modified without departing from the scope of the invention which is defined by the following claims.

What is claimed is:

1. A medical device, comprising
   an elongate and nonlinear needle having a skin piercing needle point on one end thereof,
   a protective shield operatively associated with at least a portion of said needle and adapted to be slidable along at least a portion of said needle between a needle point exposing position and a needle point protecting position wherein more of said protective shield protects said needle in the needle point protecting position than in the needle point exposing position.

2. The medical device of claim 1, wherein said protective shield includes distal and proximal sections and said distal section is movable linearly along at least a portion of said needle.

3. The medical device of claim 1, wherein said needle includes first and second needle sections which are oriented generally parallel to each other and wherein said protective shield includes a distal shield section which is movable linearly along at least a portion of said first needle section.

4. The medical device of claim 3, wherein said needle further includes an intermediate needle section wherein said intermediate needle section is nonlinearly oriented with respect to the orientation of said first and second needle sections.

5. A medical device, comprising
   an elongate nonlinear needle having distal and proximal ends and first and second needle sections and a skin piercing first needle point on said distal end of said first needle section,
   a protective shield operatively associated with said needle and adapted to be movable between a first needle point exposing position and a first needle point protecting position wherein at least a portion of said protective shield protects said needle only in the first needle point protecting position,
   a tube holding member which removably receives an evacuated tube having a sealed end in said tube holding member, and
   said second needle section being adapted to extend into at least a portion of said tube holding member and being further adapted to penetrate the sealed end of the evacuated tube upon insertion of the evacuated tube into the tube holding member.

6. The medical device of claim 5, wherein said needle is removably attachable to said tube holding member by hub member which is adapted to releasably receive said tube holding member thereon.

7. The medical device of claim 6, wherein said first and second needle sections are oriented generally parallel to each other and said hub member encloses an intermediate needle section between said first and second needle sections.

8. A medical device comprising
   an elongate needle having a distal needle point thereon and an elongate protective shield wherein one of said needle or protective shield is nonlinear with respect to the other of said needle or protective shield which is generally linear and wherein said protective shield is operatively associated with said needle and adapted to be moved between a retracted position wherein said distal needle point on said needle is exposed and an extended position wherein said distal needle point is protected and wherein more of said needle is protected by said protective shield in the extended position than in the retracted position.

9. The medical device of claim 8, wherein said needle is nonlinear and includes a first needle section with a distal portion having said distal needle point thereon and a proximal portion and said protective shield is an elongate and linear member which is oriented along said needle such that more of said protective shield extends proximally of said proximal needle portion in the retracted position than in the extended position.

10. The medical device of claim 8, wherein said protective shield is nonlinear and movable along at least a portion of said linear needle and wherein more of said protective shield extends proximally of a first needle section of said needle having said distal needle point thereon in the retracted positioned than in the extended position.

11. The medical device of claim 8, wherein a locking means is operatively associated with said protective shield to prevent the movement of said protective shield to the retracted position once said protective shield has been moved to the extended position.

12. The medical device of claim 8, wherein an elongate barrel shaped member is attachable adjacent the end of said needle opposite said distal needle point and wherein said protective shield is movable linearly along and adjacent to said barrel member as said protective shield is moved from the retracted position to the extended position.

13. The medical device of claim 8, wherein an elongate barrel shaped member is attachable adjacent the end of said needle opposite said distal needle point and wherein said protective shield is movable in a nonlinear manner with respect to the longitudinal dimension of said barrel member as said protective shield is moved from the retracted position to the extended position.

14. A medical device, comprising
a first needle section having a skin piercing first needle point thereon,
a second needle section having a stopper piercing second needle point thereon,
a hub member having said first and second needle sections mounted nonlinearly thereon, and
a protective shield slidably mounted along said hub member and adapted to be moved between a first needle point exposing position and a first needle point protecting position wherein more of said protective shield protects said needle in the needle point protecting position than in said needle point exposing position.

15. The medical device of claim 14 wherein said first and second needle sections are mounted on said needle hub in a coplanar orientation.

16. A medical device comprising
an elongate nonlinear needle having generally parallel first and second needle sections,
a skin piercing first needle point on said first needle section,
a stopper piercing second needle point on said second needle section,
a hub member substantially enclosing an intermediate needle section of said needle and said intermediate needle section being positioned in fluid communication with said first and second needle sections,
a blood collection tube holder releasably attached to said hub member at a first end and having an open second end,
a blood collection tube having a stopper thereon and wherein said blood collection tube is insertable into said second end of said blood collection tube holder so that said second needle point pierces the stopper of said blood collection tube,
an elongate protective shield slidably mounted on said hub member and adapted to be movable along said hub member between a retracted position wherein said first needle point is exposed and an extended position wherein said first needle point is protected such that more of said protective shield protects said needle in the extended position than in the retracted position, and
a locking means operatively associated with said protective shield to retain said protective shield in the extended position.

17. The medical device of claim 16, wherein said protective shield has distal and proximal ends and said distal end includes at least one tab means thereon to contact said hub member when said protective shield is in the retracted position and wherein said proximal end of said protective shield is oriented adjacent said blood collection tube holder when said protective shield is in the retracted position.

18. A medical device comprising
an elongate needle having first and second needle sections and a skin piercing needle point on said first needle section,
a hub member enclosing at least a portion of said needle between said first and second needle sections,
a blood collection tube holder releasably attached to said hub member at one end and open at the other end,
a blood collection tube having a stopper thereon wherein said second needle section pierces the stopper on said blood collection tube when said blood collection tube is inserted into said other end of said blood collection tube holder, and
a protective shield slidably mounted along said hub section wherein said protective shield is movable in a nonlinear manner with respect to said first needle section between a retracted position wherein said needle point is exposed and an extended position wherein said needle point is covered and wherein at least a portion of said protective shield moves linearly along said first needle section between the retracted and extended positions and wherein more of said protective shield protects said needle in the extended position than in the retracted position.

19. A medical device, comprising
an elongate and nonlinear needle including a first needle section having distal and proximal portions with a skin piercing needle point on the distal portion thereof;
a hub member connected to at least a portion of said needle;
a protective shield slidably supported by at least a portion of said hub member, said protective shield having distal and proximal ends and being adapted to be slidably moved between a retracted position wherein said needle point is exposed and an extended position wherein said needle point is protected by said distal end of said protective shield such that more of said protective shield protects said first needle section in the extended position than in the retracted position.

20. The medical device of claim 19 wherein said proximal end of said protective shield extends proximally from said proximal portion of said first needle section in the retracted position.

21. The medical device of claim 19 wherein said hub member includes a locking means operatively associated therewith to retrain said protective shield in the extended position.

22. The medical device of claim 19 wherein said hub member includes a retaining means operatively associated therewith to releasably retain said protective shield in an initial position wherein said needle point is exposed.

23. The medical device of claim 19 wherein said protective shield is slidably supported in a passageway in said hub member and said protective shield slides linearly between the retracted and extended positions.

24. A method of obtaining a blood sample from a patient comprising
orienting a medical device having a hub member with first and second nonlinearly oriented needle sections extending from opposite ends thereof such that a first needle point on the first needle section is aligned with the blood vessel of a patient;
piercing the blood vessel of a patient with the first needle point;
inserting a tubular member on the medical device such that a second needle point on the second needle section pierces a stopper on the tubular member to obtain a blood sample from the patient therein;
withdrawing the first needle point from the blood vessel of the patient; and
moving a protective shield which is slidably mounted along the hub member from a retracted position wherein the first needle point is exposed to an extended position wherein the first needle point is protected so that more of the protective shield protects the needle in the extended position than in the retracted position.

25. The method of claim 24 further including moving the protective shield from an initial start position wherein the first needle section is substantially enclosed by the protective shield to the retracted position prior to piercing the blood vessel of the patient with the first needle point.

26. The method of claim 24 further including locking the protective shield in the extended position so that the first needle point is protected by the protective shield.

* * * * *